United States Patent [19]

Petrov

[11] Patent Number: 5,994,599
[45] Date of Patent: Nov. 30, 1999

[54] HALOGENATED ETHERS CONTAINING FLUORINE AND PROCESSES FOR THEIR MANUFACTURE

[75] Inventor: Viacheslav Alexandrovich Petrov, Hockessin, Del.

[73] Assignee: E. I. du Pont de Nemours and Company, Wilmington, Del.

[21] Appl. No.: 09/089,893

[22] Filed: Jun. 4, 1998

Related U.S. Application Data

[60] Provisional application No. 60/050,221, Jun. 19, 1997.

[51] Int. Cl.$^6$ ................................................... C07C 21/18
[52] U.S. Cl. ............................ 570/136; 568/579; 570/142
[58] Field of Search ................................. 570/142, 136; 568/579

[56] References Cited

U.S. PATENT DOCUMENTS

| | | | |
|---|---|---|---|
| 4,357,282 | 11/1982 | Anderson et al. | 260/544 |
| 5,495,056 | 2/1996 | Burgess et al. | 570/142 |

*Primary Examiner*—Elli Peselev

[57] ABSTRACT

A process is disclosed for preparing an adduct of the formula $R^1CF_2CH_2OCF_{3-a-m}(C_2H_nX_{4-n}F)_mR^2_a$ wherein $R^1$ is selected from the group consisting of —$(CF_2)_pH$ and —$C_pF_{2p+1}$ where p is 0 or an integer from 1 to 6; $R^2$ is selected from the group consisting of —H, —$CHF_2$, —$CHFCF_3$, —$CHFOCF_3$, —$CHFO(CF_2)_2CF_3$, and —CHClF; each X is independently selected from the group consisting of Br, Cl and F; a is 0 or 1; m is 1 or 2, provided that when a is 1 and $R^2$ is other than hydrogen, then m is 1; and n is 0, 1 or 2. The process involves reacting a fluorinated ether of the formula $R^1CF_2CH_2OCF_{3-a}R^2_a$ with an olefin of the formula $C_2H_nX_{4-n}$ in the liquid phase in the presence of antimony pentafluoride catalyst. Also disclosed is a process for preparing unsaturated ethers of the formula $R^1CF_2CH_2OCF_{3-a-m}(C_2H_nX_{4-n}F)_{m-q}(C_2H_{n-1}X_{3-n}F)_qR^2_a$ wherein $R^1$, $R^2$, X, a, m, and n are as indicated above, and q is an integer from 1 to m. The process involves contacting the fluorinated ether of the formula $R^1CF_2CH_2OCF_{3-a-m}(C_2H_nX_{4-n}F)_mR^2_a$, provided that $C_2H_nX_{4-n}F$ is selected from the group consisting of —$CClFCClF_2$, —$CCl_2CCl_2F$, —$CHClCCl_2F$, —CHClCHClF and —$CCl_2CHClF$, with a dehalogenation catalyst. Certain unique saturated ethers of the formula $R^1CF_2CH_2OCF_{3-a-m}(C_2H_nX_{4-n}F)_mR^2_a$ and certain unique unsaturated ethers of the formula $R^1CF_2CH_2OCF_{3-a-m}(C_2H_nX_{4-n}F)_{m-q}(C_2H_{n-1}X_{3-n}F)_qR^2_a$ are also disclosed.

10 Claims, No Drawings

HALOGENATED ETHERS CONTAINING FLUORINE AND PROCESSES FOR THEIR MANUFACTURE

This application claims the priority benefit of U.S. Provisional Application 60/050,221, filed Jun. 19, 1997.

FIELD OF THE INVENTION

This invention relates to certain saturated and unsaturated halogenated ethers and processes for their manufacture by catalyzed addition reactions and/or catalyzed dehalogenation reactions.

BACKGROUND

Fluoroethers of the general formula R—O—CF—$R^1R^2$ have been disclosed to react in the liquid phase upon contact with a Lewis acid (e.g., $SbF_5$) to yield hydrofluorocarbons R-F (U.S. Pat. No. 5,495,056). In the α-fluoroethers of the formula R—O—CF—$R^1R^2$, the R group may generally take any form and may comprise heteroatoms (e.g., O, S or N) provided that it comprises at least one carbon atom. The R group may be saturated or unsaturated, linear or branched chain, cyclic or acyclic, aliphatic or aromatic. $R^1$ and $R^2$ are hydrogen, fluorine or optionally substituted alkyl groups. In an example, $CH_2FOCH_2F$ is reacted with $SbF_5$ at 0° C. and $CH_2F_2$ is obtained. It has also been shown that fluoroethers which contain the moieties, —$CF_2OCH_3$ or —$CF_2OC_2H_5$, react with $SbF_5$ to give compounds which do not contain ethers but instead contain a fluoroacyl (—COF) group (U.S. Pat. No. 4,357,282). In an example, $CHF_2CF_2OCH_3$ is reacted with $SbF_5$ at room temperature and $CHF_2COF$ and $CH_3F$ are isolated.

Fluorinated ethers are useful as refrigerants, heat transfer media, polymerization media, particulate removal fluids, carrier fluids, buffing abrasive agents, displacement drying agents and power cycle working fluids. Olefinic fluoroethers are useful as monomers for fluoropolymers. There is an interest in developing more efficient processes for the manufacture of fluorinated ethers.

SUMMARY OF THE INVENTION

A process is provided for preparing an adduct of the formula $R^1CF_2CH_2OCF_{3-a-m}(C_2H_nX_{4-n}F)_mR^2_a$ wherein:

$R^1$ is selected from the group consisting of —$(CF_2)_pH$ and —$C_pF_{2p+1}$ where p is 0 or an integer from 1 to 6;

$R^2$ is selected from the group consisting of —H, —$CHF_2$, —$CHFCF_3$, —$CHFOCF_3$, —$CHFO(CF_2)_2CF_3$, and —CHClF;

each X is independently selected from the group consisting of Br, Cl and F;

a is 0 or 1;

m is 1 or 2, provided that when a is 1 and $R^2$ is other than hydrogen, then m is 1; and n is 0, 1 or 2.

The process comprises reacting a fluorinated ether of the formula $R^1CF_2CH_2OCF_{3-a}R^2_a$ with an olefin of the formula $C_2H_nX_{4-n}$ in the liquid phase in the presence of antimony pentafluoride catalyst.

This invention further provides saturated ethers of said formula $R^1CF_2CH_2OCF_{3-a-m}(C_2H_nX_{4-n}F)_mR^2_a$. Included are saturated ethers of said formula where X, $R^1$, $R^2$, a, m, and n are defined as above, provided that when each X is F, a is 0, m is 1, and n is 0, then $R^1$ is other than F; and when each X is F, $R^1$ is —$(CF_2)_pH$, a is 0, m is 1 and n is 0, then p is other than 1.

This invention also provides a process for preparing unsaturated ethers of the formula $R^1CF_2CH_2OCF_{3-a-m}(C_2H_nX_{4-n}F)_{m-q}(C_2H_{n-1}X_{3-n}F)_qR^2_a$ wherein $R^1$, $R^2$, X, a, m, and n are as indicated above, and q is an integer from 1 to m. The process comprises contacting a saturated ether of the formula $R^1CF_2CH_2OCF_{3-a-m}(C_2H_nX_{4-n}F)_mR^2_a$, provided that $C_2H_nX_{4-n}F$ is selected from the group consisting of —CClFCClF$_2$, —CCl$_2$CCl$_2$F, —CHClCCl$_2$F, —CHClCHClF and —CCl$_2$CHClF, with a dehalogenation catalyst This invention still further provides unsaturated ethers of said formula $R^1CF_2CH_2OCF_{3-a-m}(C_2H_nX_{4-n}F)_{m-q}(C_2H_{n-1}X_{3-n}F)_qR^2_a$. Included are unsaturated ethers of said formula where X, $R^1$, $R^2$, a, m, n and q are as defined above, provided that when each X is F, a is 0, m is 1, n is 0 and q is 1, then $R^1$ is other than F.

DETAILED DESCRIPTION OF THE INVENTION

It has been found that surprisingly, certain fluoroethers do not decompose upon contact with the Lewis acid, $SbF_5$. Instead, the Lewis acid catalyses the addition of the fluoroether to selected olefins.

Examples of olefins of the formula $C_2H_nX_{4-n}$ which can be used to prepare adducts in accordance with one aspect of this invention include $CF_2=CF_2$, $CClF=CF_2$, $CCl_2=CF_2$, $CClF=CClF$, $CHF=CHF$, $CH_2=CF_2$, $CHF=CF_2$, $CBrF=CF_2$, $CCl_2=CCl_2$, $CHCl=CCl_2$, $CH_2=CCl_2$ and $CHCl=CHCl$. Most of the olefins are commercially available (e.g., $CH_2=CF_2$), the others can be prepared by known methods.

Certain ether starting materials which are useful in the process of this invention for preparing saturated ether adducts (e.g., $HCF_2CF_2CH_2OCF_3$, $CF_3CH_2OCHF_2$, $CF_3CH_2OCF_3$, $CF_3CHFCF_2CH_2OCF_3$ and $H(CF_2)_4CH_2OCF_3$) can be prepared by the method described in U.S. Pat. No. 5,382,704. Other ethers useful in this process, such as $CF_3CH_2OCF_2CHF_2$, $CF_3CH_2OCF_2CHFCF_3$, $CF_3CH_2OCF_2CHFOCF_3$, $CF_3CH_2OCF_2CHFOC_3F_7$ and $CF_3CH_2OCF_2CHClF$, can be prepared by the nucleophilic addition of fluoroalcohols to fluoroolefins and fluoroalkylvinyl ethers as shown in equation (1) (see Henne et al., J. Am. Chem. Soc. 72, 4378 (1950).

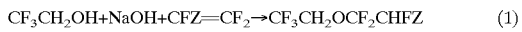

$$CF_3CH_2OH+NaOH+CFZ=CF_2 \rightarrow CF_3CH_2OCF_2CHFZ \qquad (1)$$

Z may be selected from the group consisting of —F, —$CF_3$, —$OCF_3$, —$OC_3F_7$ and —Cl. The reaction is typically done in the temperature range of 50° C. to 100° C.

Solvents or diluents may be employed for the catalyzed addition reaction of the present invention. The solvent or diluent is selected so that it will not be reactive in the process or lead to the deactivation of the antimony fluoride catalyst. Suitable solvents or diluents include those selected from the group consisting of perfluoroalkanes, (e.g., perfluorocyclobutane) the cyclic dimers of hexafluoropropene (i.e., the isomeric perfluorodimethylcyclobutanes), perfluoroethers and perfluoro tertiary amines. Preferred on the basis of its ready availability to those skilled in the art are the cyclic dimers of hexafluoropropene.

When the addition product (adduct) contains chlorine, the chlorine can be removed by either reaction with HF in the presence of a fluorination catalyst (e.g., $Cr_2O_3$) or by reaction with hydrogen in the presence of a hydrogenation catalyst (e.g., palladium supported on carbon). The adduct is thereby converted from a fluoroether containing chlorine to a fluoroether containing only hydrogen, oxygen, carbon and fluorine.

A suitable temperature range for this process of preparing saturated ether adducts is from about 0° C. to about 100° C. A preferred temperature range is from about 10° C. to 50° C.

Reaction time is not critical and typically ranges from about one hour to about 24 hours. From about 1 to 10 hours is usually sufficient.

The pressure employed for this process of preparing saturated ether adducts is not critical. The reaction is normally run at pressures in the range of about 15 to 300 psig (101 kPa to 2169 kPa). Autogenous pressures are usually employed; however, the pressure should not be allowed to rise above 300 psig (2169 kPa) when using tetrafluoroethylene because of safety considerations.

Where the reaction conditions are heterogeneous, some degree of agitation is often desirable.

Since the catalysts are water sensitive, reagents and equipment should be dried before use.

The proportion of the $SbF_5$ catalyst to the olefin reactant on a molar basis is typically about 0.5:1 to about 20:1; a range of about 1:1 to about 10:1 is preferred.

The proportion of the fluorinated ether to olefin on a molar basis is normally at least about 1:1. Of note are embodiments which use fluorinated ethers as a solvent such that they are present in substantial excess.

Examples of unique adducts which can be prepared using this invention include $HCF_2CF_2CH_2OCF(C_2F_5)_2$, (which can be prepared from $HCF_2CF_2CH_2OCF_3$ and $CF_2=CF_2$ (i.e., TFE)); $CF_3CH_2OCHFC_2F_5$ (which can prepared from $CF_3CH_2OCHF_2$ and TFE); $CF_3CH_2OCH(C_2F_5)_2$ (which can be prepared from $CF_3CH_2OCHF_2$ and TFE); $CF_3CH_2OCF(C_2F_5)CHF_2$ (which can be prepared from $CF_3CH_2OCF_2CHF_2$ and TFE); $CF_3CH_2OCF(C_2F_5)_2$ (which can be prepared from $CF_3CH_2OCF_3$ and TFE); $CF_3CHFCF_2CH_2OC_3F_7$ (which can be prepared from $CF_3CHFCF_2CH_2OCF_3$ and TFE); $CF_3CHFCF_2CH_2OCF(C_2F_5)_2$ (which can be prepared from $CF_3CHFCF_2CH_2OCF_3$ and TFE); $H(CF_2)_4CH_2OC_3F_7$ (which can be prepared from $H(CF_2)_4CH_2OCF_3$ and TFE); $H(CF_2)_4CH_2OCF(C_2F_5)_2$ (which can be prepared from $H(CF_2)_4CH_2OCF_3$ and TFE); $CF_3CH_2OCF(C_2F_5)CHFCF_3$ (which can be prepared from $CF_3CH_2OCF_2CHFCF_3$ and TFE); $CF_3CH_2OCF(C_2F_5)CHFOCF_3$ (which can be prepared from $CF_3CH_2OCF_2CHFOCF_3$ and TFE); $CF_3CH_2OCF(C_2F_5)CHFOC_3F_7$ (which can be prepared from $CF_3CH_2OCF_2CHFOC_3F_7$ and TFE); $CF_3CH_2OCF(C_2F_5)CHClF$ (which can be prepared from $CF_3CH_2OCF_2CHClF$ and TFE); $CF_3CH_2OC(C_2HF_4)_2CHF_2$ (which can be prepared from $CF_3CH_2OCF_2CHF_2$ and $CHF=CF_2$); $CF_3CH_2OCF(C_2ClF_4)CHF_2$ (which can be prepared from $CF_3CH_2OCF_2CHF_2$ and $CClF=CF_2$); $CF_3CH_2OCHFCClFCClF_2$ (which can be prepared from $CF_3CH_2OCHF_2$ and $CClF=CClF$); $CF_3CH_2OCF_2CClFCClF_2$ (which can be prepared from $CF_3CH_2OCF_3$ and $CClF=CClF$); $CF_3CH_2OCF(CClFCClF_2)CHFCF_3$ (which can be prepared from $CF_3CH_2OCF_2CHFCF_3$ and $CClF=CClF$); and $CF_3CH_2OCF(CClFCClF_2)CHFOCF_3$ (which can be prepared from $CF_3CH_2OCF_2CHFOCF_3$ and $CClF=CClF$).

Another embodiment of this invention provides a process for the dehalogenation of ethers of said formula $R^1CF_2CH_2OCF_{3-a-m}(C_2H_nX_{4-n}F)_mR^2_a$ to produce unsaturated ethers. The saturated ethers of the disclosed formula can be prepared by the same general reaction as described above. For example, a fluorinated ether of the formula $R^1CF_2CH_2OCF_{3-a}R^2_a$ can be reacted with an olefin selected from the group consisting of $CClF=CClF$, $CCl_2=CCl_2$, $CHCl=CHCl$ and $CHCl=CCl_2$ to produce the following chlorofluorinated ether adducts, $R^1CF_2CH_2OCF_{3-a-m}(C_2Cl_2F_3)_mR^2_a$, $R^1CF_2CH_2OCF_{3-a-m}(C_2Cl_4F)_mR^2_a$, $R^1CF_2CH_2OCF_{3-a-m}(C_2H_2Cl_2F)_mR^2_a$ and $R^1CF_2CH_2OCF_{3-a-m}(C_2HCl_3F)_mR^2_a$, respectively.

The dehalogenation reaction of this process (i.e., the elimination of two chlorine atoms with the formation of an olefinic bond) can be done by treating he chlorofluorinated ether adducts by procedures well known in the art. Suitable procedures include treatment with zinc metal in alcohols, ethers, dioxane or other solvents; and heterogeneous dehalogenation reactions achieved by contacting the chlorofluorinated ether adducts and hydrogen with palladium or rhenium catalysts. Respective products of the dehalogenation reaction of the above chlorofluorinated ether adducts can include $R^1CF_2CH_2OCF_{3-a-m}(CF=CF_2)_mR^2_a$, $R^1CF_2CH_2OCF_{3-a-m}(CCl=CClF)_mR^2_a$, $R^1CF_2CH_2OCF_{3-a-m}(CH=CHF)_mR^2_a$ and $R^1CF_2CH_2OCF_{3-a-m}(CH=CClF)_mR^2_a$.

Examples of unique unsaturated ethers which can be prepared using this invention include $CF_3CH_2OCHFCF=CF_2$ (which can be prepared by dechlorination of an adduct prepared from $CF_3CH_2OCHF_2$ and $CClF=CClF$); $CF_3CH_2OCF(CF=CF_2)CHFCF_3$ (which can be prepared by dechlorination of an adduct prepared from $CF_3CH_2OCF_2CHFCF_3$ and $CClF=CClF$); and $CF_3CH_2OCF(CF=CF_2)CHFOCF_3$ (which can be prepared by dechlorination of an adduct prepared from $CF_3CH_2OCF_2CHFOCF_3$ and $CClF=CClF$).

The dehalogenation reaction can be done in batch, semi-batch, semi-continuous or continuous modes in one or more reaction vessels. On a laboratory scale, the reaction can be done in shaker tubes, where all reagents are combined before the reaction vessel is sealed and the reaction begun. It can also be done in autoclaves equipped with an agitator. Product(s) may be isolated by standard chemical engineering techniques, e.g., fractional distillation.

Without further elaboration, it is believed that one skilled in the art can, using the description herein, utilize the present invention to its fullest extent. The following specific embodiments are, therefore, to be construed as merely illustrative, and does not constrain the remainder of the disclosure in any way whatsoever.

EXAMPLES

Example 1

Reaction of $HCF_2CF_2CH_2OCF_3$ With Tetrafluoroethylene (TFE)

$HCF_2CF_2CH_2OCF_3$ (50 g, 0.25 mol), $SbF_5$ (15 g, 0.07 mol) and TFE 50 g (0.5 mol) were charged into a 400 mL Hastelloy™ nickel alloy tube and agitated at 25° C. for 12 hours. The reaction mixture was poured onto ice, the organic (lower) layer was separated and dried over $P_2O_5$. Fractionation of the liquid product gave $HCF_2CF_2CH_2OCF_2CF_2CF_3$, 15.2 g (41% yield), b.p. 77.5–78° C. and $HCF_2CF_2CH_2OCF(C_2F_5)_2$, 29.3 g (57% yield), b.p. 113.5–114.5° C. (see Table 1). Polytetrafluoroethylene (PTFE), 5 g was also isolated.

Example 2

Reaction of $CF_3CH_2OCF_2H$ With Tetrafluoroethylene (TFE)

$CF_3CH_2OCF_2H$ (50 g, 0.33 mol), TFE (50 g, 0.5 mol) and $SbF_5$ (20 g, 0.09 mol) were charged into a 400 mL Hastelloy™ nickel alloy tube and agitated at 25° C. for 12 hours.

Distillation of the liquid product (58 g) gave $CF_3CH_2OCFHC_2F_5$, 34.3 g (51.5% yield based on converted starting ether), b.p. 74.8° C., and $CF_3CH_2OCH(C_2F_5)_2$ 7.8 g (33% yield), b.p. 98.8–99.2° C. (see Table 1). The formation of PTFE (25 g) was also observed.

Example 3

Reaction of $CF_3CH_2OCF_2CF_2H$ With Tetrafluoroethylene (TFE)

$CF_3CH_2OCF_2CF_2H$ (60 g, 0.3 mol), $SbF_5$ (10 g, 0.045 mol) and TFE (20 g, 0.2 mol) were charged into a 400 mL Hastelloy™ nickel alloy tube and agitated at 25° C. for 12 hours. Fractionation of the liquid product gave $CF_3CH_2OCF(C_2F_5)CF_2H$, 42 g (46.4% yield), b.p. 65.2-65.8° C. (see Table 1). No formation of PTFE was observed.

Example 4

Reaction of $CF_3CH_2OCF_2CF_2H$ With Trifluoroethylene

Trifluoroethylene (16.4 g, 0.2 mol) was bubbled through a solution of $SbF_5$ (10 g, 0.045 mol) into $CF_3CH_2OCF_2CF_2H$ (20 g, 0.1 mol) for 3 hours and the temperature maintained below 35° C. The reaction mixture was washed with water, dried and analyzed. The crude product (24 g) was a mixture containing of starting ether (8%), $CF_3CH_2OCF(CFHCF_3)CF_2H$ (10%) and $CF_3CH_2OC(CFHCF_3)_2CF_2H$ (82%) (see Table 1). The latter product (mixture of diastereomers) was isolated by distillation, b.p. 1 14–120° C., the yield was 61%.

Example 5

Reaction of $CF_3CH_2OCF_2H$ With $CFCl=CFCl$ $CFCl=CFCl$ (25 g, 0.2 mol) was added dropwise over the course of an hour to a stirred mixture of $CF_3CH_2OCF_2H$ (50 g, 0.33 mol) and $SbF_5$ (8 g, 0.037 mol) at 10–20° C. The reaction mixture was stirred for another 30 minutes at room temperature after the addition was finished. It was then poured onto ice and the organic layer was separated, dried over $P_2O_5$ and distilled to give $CF_3CH_2OCFHCFClCF_2Cl$ (mixture of diastereomers) 25 g (43%), b.p. 55–58° C./25 mm Hg (3.3 kPa) (see Table 1).

Example 6

Preparation of $CF_3CH_2OCF(CF=CF_2)CFHCF_3$

A mixture of Zn dust (7 g), $C_2H_5OH$ (50 mL) and $CF_3CH_2OCF(CFClCF_2Cl)CFHCF_3$ (15 g) was heated at reflux for 1 hour. The reaction mixture was cooled to 25° C., decanted and the solid washed twice with alcohol. The combined solution was poured into diluted (5%) hydrochloric acid and the organic layer was separated, washed with water, dried over $P_2O_5$ and distilled to give $CF_3CH_2OCF(CF=CF_2)CFHCF_3$ 10 g (83%) (see Table 1.)

Comparative Example A

Reaction of $ClCF_2CH_2OCF_2CF_2H$ With $SbF_5$ $ClCF_2CH_2OCF_2CF_2H$ (3 mmol) was slowly added to a solution of $SbF_5$ (2 g) in $SO_2ClF$ (12 mmol) at −78° C. The reaction mixture was mixed by shaking and analyzed by $^{19}F$ NMR at −40° C. After 20 minutes the reaction mixture did not contain any of the starting ether, but only $CF_3H$ and $CF_3CH_2Cl$ in a 1:1 molar ratio.

Comparative Example B

Reaction of $C_3F_7OCHFCF_3+TFE+SbF_5$

The apparatus and procedure of Example 1 was used. $C_3F_7OCHFCF_3$ (200 g) was contacted with TFE (30 g) in the presence of $SbF_5$ (10 g) at 25° C. for 12 hours. No condensation product was found in the crude reaction mixture. The starting ether (60%) was recovered along with PTFE (25 g).

The results obtained from Comparative Examples A and B contrast with the results of reactions in accordance with this invention which form adducts rather than degradation products. Additional examples of reactions in accordance with the present invention (Nos. 7 through 18) are summarized in Table 1.

TABLE 1

Condensation of Polyfluorinated Ethers with Fluoroolefins Catalyzed by $SbF_5$

| Ex. No. | $SbF_5$ (wt. %) | Reactants (mol. ratio) | Temp (° C.) Time (h) | Products (% yield) | b.p. (° C.) | Anal. or MS found (calcd.) |
|---|---|---|---|---|---|---|
| 1 | 13 | $HCF_2CF_2CH_2OCF_3$ + TFE(1:2) | 25(12) | $HCF_2CF_2CH_2OC_3F_7$ (41), | 77.5–77.9 | C, 23.13 (24.00); H, 0.99 (1.00); F, 69.85 (69.67) |
|   |    |                                  |        | $HCF_2CF_2CH_2OCF(C_2F_5)_2$(57) | 113.5–114.5 | C, 22.96 (24.00) H,0.74 (0.75); F, 72.36 (71.25) |
| 2 | 17 | $CF_3CH_2OCF_2H$ + TFE (3:2) | 25(12) | $CF_3CH_2OCFHC_2F_5$ (52) | 74.8 | C, 23.34 (24.00); H, 1.19 (1.20); F, 69.78 (68.40) |
|   |    |                              |        | $CF_3CH_2OCH(C_2F_5)_2$(33) | 99.2 | C, 23.43 (24.00); H, 0.87 (0.86); F, 72.29 (70.57) |
| 3 | 11 | $CF_3CH_2OCF_2CF_2H$ + TFE (3:2) | 25(14) | $CF_3CH_2OCF(C_2F_5)CF_2H$ (70) | 65.2–65.8 | C, 23.81 (24.00); H, 0.99 (1.00); F, 69.97 (69.67) |
| 4 | 20 | $CF_3CH_2OCF_2CF_2H$ + $C_2F_3H^a$ (1:2) | 25–30(4) | $CF_3CH_2OC(CFHCF_3)_2CF_2H$(61) | 114–120 | C, 26.47 (26.37); H, 1.58 (1.37); F, 69.26 (67.86) |
| 5 | 10 | $CF_3CH_2OCF_2H$ + $C_2F_2Cl_2^b$ (3:2) | 10–30 (3) | $CF_3CH_2OCFHCFClCF_2Cl$ (43) | 55.7–56.7/25 mm (3.3 kPa) | C, 20.98 (21.20); H, 0.90 (1.06); F, 47.11 (46.97); Cl, 24.82 (25.09) |
| 6 | — | $CF_3CH_2OCF(CFCl-CF_2Cl)CFHCF_3$ + Zn + $C_2H_5OH$ | reflux | $CF_3CH_2$—$OCF(CF=CF_2)$-$CFHCF_3$ (83) | 108–110 | C, 26.72 (26.92); H, 0.96 (1.09); F, 66.63 (66.98) |
| 7 | 5 | $CF_3CH_2OCF_3$ + TFE(3:2) | 25 (12) | $CF_3CH_2OC_3F_7$(5), $CF_3CH_2OCF(C_2F_5)_2$(9) | — | — |

TABLE 1-continued

Condensation of Polyfluorinated Ethers with Fluoroolefins Catalyzed by SbF$_5$

| Ex. No. | SbF$_5$ (wt. %) | Reactants (mol. ratio) | Temp (° C.) Time (h) | Products (% yield) | b.p. (° C.) | Anal. or MS found (calcd.) |
|---|---|---|---|---|---|---|
| 8 | 8 | CF$_3$ CFHCF$_2$CH$_2$OCF$_3$ + TFE(1:1) | 25 (12) | CF$_3$ CFHCF$_2$CH$_2$OCF$_2$-C$_2$F$_5$(10) | 125 | — |
| | | | | CF$_3$ CFHCF$_2$CH$_2$OCF-(C$_2$F$_5$)$_2$(50) | — | — |
| 9 | 16 | H(CF$_2$CF$_2$)$_2$CH$_2$OCF$_3$ + TFE(1:1) | 25 (12) | H(CF$_2$CF$_2$)$_2$CH$_2$O—C$_3$F$_7$ (10) | — | m/e (M-F) 380.9983 (380.9960) |
| | | | | H(CF$_2$CF$_2$)$_2$CH$_2$O—CF-(C$_2$F$_5$)$_2$(6.8) | — | m/e (M-F) 480.9973 (489.9996) |
| 10 | 11 | CF$_3$CH$_2$OCF$_2$CF$_2$H + C$_2$F$_3$Cl$^c$ (1:1) | 25 (14) | CF$_3$CH$_2$OCF(C$_2$F$_4$Cl)-CF$_2$H$^d$ (48) | 72–75 | C, 22.76 (22.75); H, 0.95 (1.14); F, 60.25 (60.03) |
| 11 | 9 | CF$_3$CH$_2$OCF$_2$CFHCF$_3$ + TFE (1:1) | 25 (14) | CF$_3$CH$_2$OCF(C$_2$F$_5$)-CFHCF$_3$ (57.5) | 90.3–91 | C, 23.85 (24.00); H, 0.86 (1.01); F, 69.18 (70.07) |
| 12 | 6 | CF$_3$CH$_2$OCF$_2$CFHO-CF$_3$ + TFE (1:1) | 25 (14) | CF$_3$CH$_2$—OCF(C$_2$F$_5$)-CFHOCF$_3$ (42) | 98–99 | C, 21.71 (22.95); H, 0.90 (0.82); F, 67.67 (67.49) |
| | | | | C$_8$H$_3$F$_{13}$O$_2{}^e$ (6.2) | 112 | C, 24.16 (25.41); H, 0.78 (0.80); F, 66.73 (65.34) m/e. 377.9883 (377.9925) |
| 13 | 7 | CF$_3$CH$_2$OCF$_2$CFHO-C$_3$F$_7$ + TFE(1:1) | 25 (14) | CF$_3$CH$_2$OCF(C$_2$F$_5$)-CFHOC$_3$F$_7$(22) | 122–126 | m/e 446.9842(446.9878) |
| 14 | 16 | CF$_3$CH$_2$OCF$_2$CFClH + TFE(1:1) | 25 (14) | CF$_3$CH$_2$OCF(C$_2$F$_5$)-CFClH(62) | 106–109 | — |
| 15 | 10 | CF$_3$CH$_2$OCF$_2$CF$_2$H + C$_2$F$_2$Cl$_2$(1:1) | 10–35 | CF$_3$CH$_2$OCF(CFCl-CF$_2$Cl)CF$_2$H(53) | 50–51/25 mm (3.3 kPa) | C, 22.70 (22.77); H, 0.97 (0.96); Cl, 11.45 (11.20) |
| 16 | 6 | CF$_3$CH$_2$OCF$_3$ + C$_2$F$_2$Cl$_2$(2:1) | 10–20 | CF$_3$CH$_2$OCF$_2$CFCl-CF$_2$Cl(17)$^f$ | — | C, 21.77 (21.64); H, 1.05 (0.91) |
| 17 | 6 | CF$_3$CH$_2$OCF$_2$CFHCF$_3$ + C$_2$F$_2$Cl$_2$(2:1) | 10–25 | CF$_3$CH$_2$OCF(CFClCF$_2$Cl)CFHCF$_3$ (42%) | 55–56.4/25 mm (3.3 kPa) | C, 21.15 (21.95); H, 0.82 (0.79); F, 54.34 (54.57); Cl, 19.29(18.51) |
| 18 | 7 | CF$_3$CH$_2$OCF$_2$CFHO-CF$_3$ + C$_2$F$_2$Cl$_2$(2:1) | 10–15° C. | CF$_3$CH$_2$OCF(CFCl-CF$_2$Cl)CFHO—CF$_3$ (43%) | 54–57/25 mm (3.3 kPa) | C, 21.22 (21.07); H, 0.67 (0.76) |

$^a$CFH=CF$_2$
$^b$CFCl=CFCl
$^c$CF$_2$=CFCl
$^d$mixture of isomers CF$_3$CH$_2$OCF(CFClCF$_3$)CF$_2$H and CF$_3$CH$_2$OCF(CF$_2$CF$_2$Cl)CF$_2$H in ratio 69:31
$^e$
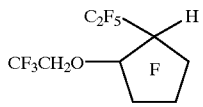

$^f$yield is based on NMR data

I claim:

1. A process for preparing an adduct of the formula R$^1$CF$_2$CH$_2$OCF$_{3-a-m}$(C$_2$H$_n$X$_{4-n}$F)$_m$R$^2{}_a$ wherein R$^1$ is selected from the group consisting of —(CF$_2$)$_p$H and —C$_p$F$_{2p+1}$ where p is 0 or an integer from 1 to 6; R$^2$ is selected from the group consisting of —H, —CHF$_2$, —CHFCF$_3$, —CHFOCF$_3$, —CHFO(CF$_2$)$_2$CF$_3$, and —CHClF; each X is independently selected from the group consisting of Br, Cl and F; a is 0 or 1; m is 1 or 2, provided that when a is 1 and R$^2$ is other than hydrogen, then m is 1; and n is 0, 1 or 2, comprising:

reacting a fluorinated ether of the formula R$^1$CF$_2$CH$_2$OCF$_{3-a}$R$^2{}_a$ with an olefin of the formula C$_2$H$_n$X$_{4-n}$ in the liquid phase in the presence of antimony pentafluoride catalyst.

2. The process of claim 1 wherein HCF$_2$CF$_2$CH$_2$OCF$_2$CF$_2$CF$_3$ is prepared by reacting HCF$_2$CF$_2$CH$_2$OCF$_3$ with C$_2$F$_4$.

3. A saturated ether of the formula:

R$^1$CF$_2$CH$_2$OCF$_{3-a-m}$(C$_2$H$_n$X$_{4-n}$F)$_m$R$^2{}_a$ wherein R$^1$ is selected from the group consisting of —(CF$_2$)$_p$H and —C$_p$F$_{2p+1}$ where p is 0 or an integer from 1 to 6; R$^2$ is selected from the group consisting of —H, —CHF$_2$, —CHFCF$_3$, —CHFOCF$_3$, —CHFO(CF$_2$)$_2$CF$_3$, and —CHClF; each X is independently selected from the group consisting of Br, Cl and F; a is 0 or 1; m is 1 or 2, provided that when a is 1 and R$^2$ is other than hydrogen, then m is 1; and n is 0, 1 or 2;

provided that when each X is F, a is 0, m is 1, and n is 0, then R$^1$ is other than F; and when each X is F, R$^1$ is —(CF$_2$)$_p$H, a is 0, m is 1 and n is 0, then p is other than 1.

4. A saturated ether of claim 3 selected from the group consisting of HCF$_2$CF$_2$CH$_2$OCF(C$_2$F$_5$)$_2$, CF$_3$CH$_2$OCHFC$_2$F$_5$, CF$_3$CH$_2$OCH(C$_2$F$_5$)$_2$, CF$_3$CH$_2$OCF(C$_2$F$_5$)CHF$_2$, CF$_3$CH$_2$OCF(C$_2$F$_5$)$_2$, CF$_3$CHFCF$_2$CH$_2$OC$_3$F$_7$, CF$_3$CHFCF$_2$CH$_2$OCF(C$_2$F$_5$)$_2$, H(CF$_2$)$_4$CH$_2$OC$_3$F$_7$, H(CF$_2$)$_4$CH$_2$OCF(C$_2$F$_5$)$_2$, CF$_3$CH$_2$OCF(C$_2$F$_5$)CHFCF$_3$, CF$_3$CH$_2$OCF(C$_2$F$_5$)CHFOCF$_3$, CF$_3$CH$_2$OCF(C$_2$F$_5$)CHFOC$_3$F$_7$, CF$_3$CH$_2$OCF(C$_2$F$_5$)CHClF, CF$_3$CH$_2$OC(C$_2$HF$_4$)$_2$CHF$_2$, CF$_3$CH$_2$OCF(C$_2$ClF$_4$)CHF$_2$, CF$_3$CH$_2$OCHFCClFCClF$_2$, CF$_3$CH$_2$OCF$_2$CClFCClF$_2$, CF$_3$CH$_2$OCF(CClFCClF$_2$)CHFCF$_3$, and CF$_3$CH$_2$OCF(CClFCClF$_2$)CHFOCF$_3$.

5. A process for preparing unsaturated ethers of the formula R$^1$CF$_2$CH$_2$OCF$_{3-a-m}$(C$_2$H$_n$X$_{4-n}$F)$_{m-q}$(C$_2$H$_{n-1}$X$_{3-n}$F)$_q$R$^2{}_a$ wherein R$^1$ is selected from the group consisting of —(CF$_2$)$_p$H and —C$_p$F$_{2p+1}$ where p is 0 or an integer from 1 to 6; R$^2$ is selected from the group consisting of —H, —$CHF_2$, —$CHFCF_3$, —$CHFOCF_3$, —$CHFO(CF_2)_2CF_3$, and —$CHClF$; each X is independently selected from the group consisting of Br, Cl and F; a is 0 or 1; m is 1 or 2, provided that when a is 1 and $R^2$ is other than hydrogen, then m is 1; n is 0, 1 or 2; and q is an integer from 1 to m, comprising:

contacting a saturated ether of the formula $R^1CF_2CH_2OCF_{3-a-m}(C_2H_nX_{4-n}F)_mR^2{}_a$, provided that $C_2H_nX_{4-n}F$ is selected from the group consisting of—$CClFCClF_2$, —$CCl_2CCl_2F$, —$CHClCCl_2F$, —$CHClCHClF$ and —$CCl_2CHClF$, with a dehalogenated catalyst.

6. The process of claim 5 wherein $CF_3CH_2OCF(CF=CF_2)CFHCF_3$ is prepared by reacting $CF_3CH_2OCF(CFClCF_2Cl)CFHCF_3$.

7. The process of claim 5 wherein the saturated ether is prepared by reacting a fluorinated ether of the formula $R^1CF_2CH_2OCF_{3-a}R^2{}_a$ with an olefin of the formula $C_2H_nX_{4-n}$ in the liquid phase in the presence of antimony pentafluoride catalyst.

8. The process of claim 7 wherein $CF_3CH_2OCF(CFClCF_2Cl)CFHCF_3$ is prepared by reacting $CF_3CH_2OCF_2CFHCF_3$ with $C_2F_2Cl_2$; and $CF_3CH_2OCF(CF=CF_2)CFHCF_3$ is prepared by dechlorination of said $CF_3CH_2OCF(CFClCF_2Cl)CFHCF_3$.

9. An unsaturated ether of the formula:

$$R^1CF_2CH_2OCF_{3-a-m}(C_2H_nX_{4-n}F)_{m-q}(C_2H_{n-1}X_{3-n}F)_qR^2{}_a$$

wherein $R^1$ is selected from the group consisting of—$(CF_2)_pH$ and —$C_pF_{2p+1}$ where p is 0 or an integer from 1 to 6; $R^2$ is selected from the group consisting of —H, —$CHF_2$, —$CHFCF_3$, —$CHFOCF_3$, —$CHFO(CF_2)_2CF_3$, and —$CHClF$; each X is independently selected from the group consisting of Br, Cl and F; a is 0 or 1; m is 1 or 2, provided that when a is 1 and $R^2$ is other than hydrogen, then m is 1; n is 0, 1 or 2; and q is an integer from 1 to m;

provided that when each X is F, a is 0, m is 1, n is 0 and q is 1, then $R^1$ is other than F.

10. An unsaturated ether of claim 9 selected from the group consisting of $CF_3CH_2OCHFCF=CF_2$, $CF_3CH_2OCF(CF=CF_2)CHFCF_3$, and $CF_3CH_2OCF(CF=CF_2)CHFOCF_3$.

* * * * *